United States Patent
Hitchens et al.

(10) Patent No.: US 6,265,205 B1
(45) Date of Patent: Jul. 24, 2001

(54) ENHANCEMENT OF SOIL AND GROUNDWATER REMEDIATION

(75) Inventors: G. Duncan Hitchens, Bryan; Drahomira Brejchova, Sugar Land; Alan J. Cisar, Cypress; Dalibor Hodko, College Station; Oliver J. Murphy, Bryan, all of TX (US)

(73) Assignee: Lynntech, Inc., College Station, TX (US)

( * ) Notice: Subject to any disclaimer, the term of this patent is extended or adjusted under 35 U.S.C. 154(b) by 0 days.

(21) Appl. No.: 09/013,729

(22) Filed: Jan. 27, 1998

(51) Int. Cl.[7] .................................................. C12S 13/00
(52) U.S. Cl. .................. 435/262; 435/262.5; 166/246
(58) Field of Search .................. 435/262, 262.5; 588/205, 206, 207; 405/128, 263, 129; 166/246, 309; 208/262.1, 262.5

(56) References Cited

U.S. PATENT DOCUMENTS

| | | | |
|---|---|---|---|
| 2,623,812 | * | 12/1952 | Eborall et al. . |
| 3,942,511 | * | 3/1976 | Black et al. . |
| 3,957,483 | * | 5/1976 | Suzuki . |
| 3,982,592 | * | 9/1976 | Hamrick et al. . |
| 4,017,414 | | 4/1977 | Black et al. . |
| 4,264,362 | * | 4/1981 | Sergev et al. . |
| 5,478,452 | * | 12/1995 | Chriswell et al. . |
| 5,510,201 | * | 4/1996 | Werth . |
| 5,602,296 | * | 2/1997 | Hughes et al. . |
| 5,810,514 | * | 9/1998 | Suchecki, Jr. ........................ 405/128 |

OTHER PUBLICATIONS

Distefano et al.'Hydrogen as an Electron Donor for Dechlorination of Tetrachloroethene by an anaerobic mixed culture.' Applied and Environmental Microbiology. vol. 58, No. 11 (Nov. 1992), pp. 3622–3629.*

Holliger et al. 'A highly purified enrichment culture couples the reductive dechlorination of tetrachloroethene to growth.' Applied and Environmental Microbiology. vol. 59, No. 9 (Sep. 1993), pp. 2991–2997.*

Larry Montgomery, Nada Assaf–Anid, Loring Nies, Paul J. Anid, and Timothy M. Vogel, Anaerobic Biodegradation of Chlorinated Organic Compounds, pp. 256–276.

Richard S. Hanson and Gregory A. Brusseau, "Biodegradation of Low–Molecular–Weight Halogenated Organic Compound by Aerobic Bacteria, "pp. 277–297.

* cited by examiner

Primary Examiner—William H. Beisner
(74) Attorney, Agent, or Firm—Streets & Associates; Jeffrey L. Streets

(57) ABSTRACT

This invention is a novel method for bioremediation of soil and ground water based on supplying hydrogen ($H_2$) to naturally occurring anaerobic bacteria in the soil or ground water. These organisms use the hydrogen as an electron donor to perform adventitious chemical reactions including the dehalogenation of chlorinated organic compounds. The hydrogen can be supplied from a number of sources, including; stored hydrogen, hydrogen generated above ground on site, either electrochemically or by reforming a fuel source, or by electrolysis in the soil, either using an electric current supplied from above ground or an electric current generated by the corrosion of metal particles in the ground. For the last of these cases, a novel multi-metallic particle especially useful for the generation of hydrogen, and a method for making these particles, are disclosed.

44 Claims, 4 Drawing Sheets

ENHANCEMENT OF SOIL AND GROUNDWATER REMEDIATION

This invention was made with government support under contracts NAS10-12168, NAS10-98033 and NAS10-12266 awarded by NASA. The government has certain rights in this invention.

FIELD OF THE INVENTION

This invention relates to the field of bioremediation of contaminated environments. The invention particularly relates to a method for enhancing the biodegradation of chlorinated organic compounds in the ground by naturally occurring bacteria.

BACKGROUND OF THE INVENTION

Insecticides, polychlorinated biphenyls (PCBs), chlorinated benzenes, chlorophenols, chloroquaiacols, chloroveratroles, chlorocatechols, as well as chlorinated aliphatics are contaminants whose toxicity can be decreased or eliminated by reductive dechlorination. This process involves the successive shedding of chlorine atoms under reduced anaerobic conditions and is usually biologically catalyzed.

Chlorinated ethenes (unsaturated $C_2$ compounds), such as tetrachloroethylene ($C_2Cl_4$) and trichloroethylene ($C_2HCl_3$) are among the most frequently found contaminants in soils and aqueous environments. These contaminants, generally released from industrial and commercial sources, have become a ubiquitous presence in many ecosystems. Wide spread occurrence of chlorinated ethenes in the environment is of great concern due to their toxicity, carcinogenicity and persistence in the environment. Along with other low molecular-weight halogenated organic compounds, chlorinated ethenes are listed by the United States Environmental Agency as high priority pollutants.

Various factors complicate the removal of these contaminants from the environment. They are exceedingly volatile, highly mobile, denser than water, and generally found in the environment as mixtures of products with different degrees of chlorination. In addition, when these contaminants are present in soil, contamination is generally so extensive that excavation is impractical and cost prohibitive.

While removal of chloroethenes by pump and treat methods may offer a less costly alternative, these methods are just as impractical as excavation. In situ processes based on extraction, stripping, and/or adsorption on activated carbon can also remove chloroethene pollutants but these processes do not solve the problem of final disposal. Thus, much effort has been devoted to the development of practical and cost effective techniques for the removal of chlorinated contaminants from the environment, particularly from contaminated soils.

Bioremediation may offer a practical alternative for the removal of chlorinated contaminants from the environment. But for bioremediation techniques to be fully effective, significant progress must be made in enhancing the kinetics of the complex chemical processes underlying bioremediation.

For chlorinated ethenes in soil, recalcitrance in the presence of oxygen can be alleviated during co-metabolic degradation in aerobic environments by delivering natural gas or methane to the subsurface. In this context, methane serves as a carbon rich energy source for methanotrophic bacteria which also coincidentally metabolize some chlorinated contaminants. Under anaerobic conditions, all chlorinated ethenes can be completely transformed into benign end products through sequential reductive dechlorination. In this biologically catalyzed process, chlorinated pollutants act as electron acceptors, the chloride moiety is removed from molecules and replaced by hydrogen. The availability of a suitable electron donor for this process is one of the key rate limiting elements.

Transformation of perchloroethylene (PCE) proceeds by sequential reductive dechlorination to trichloroethylene (TCE), dichloroethylenes (DCEs), vinyl chloride (VC), and ethylene (ETH). ETH is a commonly occurring plant hormone that has not been associated with any long-term toxicological problems.

FIG. 1 is a schematic diagram of the conversion pathway from PCE to ETH. The diagram shows two of the three possible DCE isomers. 1,1-DCE is the less significant isomer and is not shown. Cis-1,2-DCE predominates over trans-1,2-DCE.

The rates of reductive dechlorination reactions are a function of the chemical structure of the chlorinated compound. Highly chlorinated, and consequently highly oxidized, ethenes are rapidly dechlorinated via this process, while less substituted ethenes are more resistant to reduction. Consequently the rate-limiting step in reductive dechlorination is the conversion of VC to ETH. ETH is considered an end product although further degradation of ETH to $CO_2$ may occur. Such degradation is thought to be hindered by the observed recalcitrance of ETH attributed to its role as a potent selective inhibitor of methanogenesis.

Sustaining reductive dechlorination is highly dependent upon the availability of an electron donor (reductant) in the contaminated environment. Some of the compounds that have been found to support the reductive transformation of PCE are glucose, acetate, formate, methanol, lactate, propionate, crotonate, butyrate, ethanol, and other compounds such as toluene and dichloromethane. Higher dechlorinating activities were observed when organic substrates that contain more reducing power during anaerobic digestion (e.g. formate, glucose, lactate) were used. Also, electron donors that produce hydrogen more slowly give a selective advantage to organisms that dechlorinate chlorocarbons over those that generate methane. Thus, It would be highly desirable to provide a method that uses hydrogen as the direct electron donor in the removal of chlorinated compounds through the process of reductive dechlorination.

FIG. 2 is a graph showing the influence on PCE degradation when hydrogen is added to the system. The graph shows that PCE degradation is substantially higher in cultures supplied with hydrogen compared to cultures not supplied with hydrogen. The slow degradation of PCE in the absence of added hydrogen is probably supported by the yeast extract initially present in the basal medium.

At the mechanistic level, reductive dechlorination is a biologically catalyzed chemical process. Reductive dechlorination occurs readily in a variety of complex anaerobic communities without acclimation, or with relatively short acclimation times (less than 1 month). This suggests that the catalyst is non-specific and continuously present in the natural community. Transition metal complexes (porphyrins), common to many enzymes, have been found to be involved in these processes. For example, vitamin $B_{12}$ (Co-containing porphyrin) which is often found in bacteria, and coenzyme $F_{430}$ (Ni-containing porphyrin), found only in methanogenic bacteria, have the capacity to mediate the eight-electron sequential reduction of PCE to ETH.

The roles played by major classes of microorganisms inhabiting mixed cultures capable of dechlorinating synthetic compounds are still not exactly known. The hypothesis that the dechlorinating organisms are hydrogen utilizers that are nutritionally dependent on other organisms in the more diverse system has been examined. It is suggested that methanogens play a key role in the process. For example, degradation of TCE was completely stopped when bromoethane sulfonate (a selective inhibitor of methyl-coenzyme-M reductase which catalyzes the final step in methanogenesis) was added to mixed cultures. On the other hand sustained dechlorination in the presence of vancomycin which inhibits acetogenesis suggests that acetogens are probably not the dechlorinators.

Direct dechlorinators that utilize chlorinated ethenes as electron acceptors in an energy-conserving, growth-coupled metabolism termed dehalospiration may also contribute to the process of reductive dechlorination. These microorganisms must compete for available hydrogen with hydrogenotrophic methanogens and sulfate reducers and because of the relatively high energy available from reductive dechlorination, it is reasonable to suspect that they may out-compete methanogens at very low hydrogen levels. Competition for hydrogen is thus a very important aspect of the reductive dechlorination process. The partitioning of hydrogen flows among the various competitors is a function of the hydrogen concentration, which itself depends on the rates of hydrogen production and utilization.

Compounds such as lactate or ethanol that can be rapidly fermented to acetate, producing high short-lived peaks of hydrogen, do not favor dechlorination as well as would more persistent, slowly fermented substrates such as benzoate or propionate. Thus it would be highly desirable to design new techniques and methods that would allow slow $H_2$ release, closely matching the rate of metabolic uptake by the dechlorinators. Such techniques and methods would allow a significant increase in the rate of in situ degradation of chlorinated pollutants.

Chlorinated solvents, such as trichloroethylene and perchloroethylene can be degraded by reactions with granular iron. This abiotic reductive dehalogenation is thought to proceed with pseudo-first order kinetics. Although details of the chemical mechanisms involved in this process are yet to be fully elucidated, the process is thought to involve the simultaneous oxidative corrosion of the reactive iron metal by both water and the chlorinated organic compounds. The two half-reactions involving iron and TCE can be shown as:

$$Fe^{\circ} \rightarrow Fe^{2+} + 2e^{-} \qquad (1)$$

$$C_2HCl_3 + 3H^+ + 6e^- \rightarrow C_2H_4 + 3Cl^- \qquad (2)$$

These are accompanied by the decomposition of water and subsequent formation of hydrogen gas:

$$2H_2O + 2e^- \rightarrow H_2(g) + 2OH^- \qquad (3)$$

This chemical degradation process is assisted by a parallel biological route where the growth of methanogenic bacteria is stimulated by the produced hydrogen, and these organisms enzymatically dechlorinating additional contaminants.

Bimetallic preparation of iron with a small amount of Pd (0.05% by weight) can substantially enhance the dechlorination rate of volatile organic compounds. Similarly, adding a nickel coating to iron particles greatly enhances the dechlorination kinetics of many chlorinated VOCs, typically by an order of magnitude over reduction by iron alone. Both palladium and nickel enhance the generation of hydrogen gas, as described below. As suggested by equation (2), TCE degrades spontaneously in the presence of both water and iron, requiring no additives or application of energy, and the products of the chlorinated compounds are chloride and nontoxic hydrocarbons. The method offers a "passive treatment method" which can produce a substantial cost reduction in anticipated operation and maintenance expenses for a remediation project.

The very low levels at which toxicants are present in ground water is a factor in designing suitable treatment systems. Although the quantity of reductant that meets the stoichiometric requirements is small, a large excess of iron is required to provide a reactive surface area large enough for the contaminants to adsorb on the surface and the reaction to occur. Lengthy "flow-through" times (i.e., residence times) are also needed. Usually, treatment zones are created by forming a fixed bed reactive barrier, of either a continuous wall or funnel-and-gate type system. In either case, iron is placed deep enough to intercept the saturated thickness of the plume in a contaminated zone. Sometimes above ground reactors are used. The rates of dehalogenation vary widely for the various chlorinated solvents of interest, and when the design of a treatment method includes a mixture, the design of a barrier is determined by the least reactive constituent. Rate constants normalized to iron surface area have been used as the basis for barrier design and size considerations. For example, a model for calculating the amount of iron needed for 1000 fold decrease in contaminants has been developed. With the unit cost of granulated iron at approximately $450/ton, the amount of iron required represents a substantial cost. Even modest sized treatment barriers, 2 ft (w)×100 ft (l)×50 ft (d), that would be capable of treating ground water flow velocity of no greater than 1 ft/day, would cost nearly $1 million in granulated iron alone. Thus, potential operating and maintenance cost advantages of reactive metal barriers are in some ways offset by high installation costs. Furthermore, the method is complicated by the need to ensure that the ground water is directed through the barrier and to avoid the possibility of flow around the edges. Another limitation of these techniques is related to the clogging that may occur with long term use of zero-valent iron, thus it is expected that the surface will require regeneration, an issue that has been given little attention at the present time.

U.S. Pat. No. 5,510,201 discloses a hydrogen producing system that utilizes corrosion of iron by water. The disclosed system invokes the potential benefit for regenerating iron subsequent to corrosion. The invoked methods for regenerating iron are, however, limited to chemical treatment by providing reforming fuels to the corroded iron. Such treatments necessitate the collection of the corroded iron for delivery to central plants where it would be regenerated. Such regeneration techniques are impractical in the context of contaminated environment bioremediation.

U.S. Pat. No. 2,623,812 discloses a hydrogen production system based on the use of metal particles combining iron and magnesium. The combination is obtained by mixing powders of iron and magnesium. While the disclosed combinations yield some enhancement in the rate of hydrogen production, the maximum improvement that can be obtained through this technique is drastically limited by the method of preparation of the metallic combination. More intimate combination of the metals is particularly desirable in the context of bioremediation of contaminated soils which require the production of significant quantities of hydrogen for extended periods of time.

In U.S. Pat. No. 3,942,511, Black et al. recognized the need for higher intimacy between iron and magnesium for a combination of the metals to yield higher rates of hydrogen production. Their proposed method for achieving higher intimacy between the metals is based on improved contact between the metal particles, achieved through compressing of the particles. Black et al. also disclose the need in their method for adding salts to the metal combination in order to achieve a higher contact between the metals.

U.S. Pat. No. 4,264,362 also discloses a mechanically based metal mixing technique for the formation of bimetallic particles with higher dispersion of smaller particles of one metal in larger particles of another metal.

In U.S. Pat. No. 3,957,483, Suzuki discloses a method for enhancing hydrogen production by corroding iron. His method is also mechanically based. Iron particles are mechanically attached to magnesium particles.

While the above described attempts seem to recognize the need for a higher degree of intimacy in combining iron and magnesium to increase the rates of hydrogen production, all the disclosed techniques are limited to one version or another of mechanically mixing the metals. The degree of intimacy obtainable through any mechanical mixing method is inherently limited by the size of the smallest particle obtainable by mechanically disintegrating a larger metal particle. Thus, in hydrogen production by corrosion of a metallic particle, multi-metallic particles with degrees of intimacy beyond what can be achieved through mechanical mixing are highly desirable. Such particles are particularly desirable in applications that necessitate the production of high quantities of hydrogen for long periods of time such as bioremediation of contaminated soils.

SUMMARY OF THE INVENTION

The present invention provides a method for enhancing the rate of biodegradation of chlorinated organic compounds in contaminated environments by providing hydrogen to the environment and stimulating the anaerobic growth of microorganisms therein. In one embodiment of the invention, hydrogen is provided to contaminated soil through an above ground hydrogen source. The invention provides for a variety of sources of hydrogen. The hydrogen source may comprise a gas storage system. The hydrogen source may also be a hydrogen generator. Hydrogen generators that can be used in conjunction with this invention comprise electrochemical devices such as electrolyzers, carbonaceous-fuel reforming systems such as a steam reformer, a partial combustion cracker, or an autothermal reformer. In one particular embodiment, the carbonaceous fuel is produced through the degradation of waste material.

In yet another aspect of the present invention, the hydrogen is generated in the soil subjected to decontamination. The invention provides several methods and techniques for the generation of hydrogen in the soil. It can be easily appreciated by those skilled in the art that variations of the methods described here as well as other related techniques for the generation of hydrogen in the soil are within the scope of the present invention.

One of the methods provided by the present invention for the generating of hydrogen in the soil comprises electrochemical generation of hydrogen by supplying an electric field to the soil.

Another method provided by this invention is based on generating hydrogen in situ by corroding metal particles inserted in the soil. The metal particles that can be used in conjunction with the present invention comprise but are not limited to metal particles that consist of two or more metal components. In one embodiment of the present invention, the metal particles are loosely dispersed in the contaminated soil. In another embodiment, the metal particles are retained in a porous medium.

In yet another embodiment of the invention, the metal particle comprises a metal component with higher activity in oxidation by water and at least one metal component with lower activity in oxidation by water. Hydrogen is generated by contacting said metal particle with water or another electrolyte comprising water. In a preferred embodiment of the invention, the metal particle with higher activity in oxidation by water is corroded causing the metal component with lower activity in oxidation by water to be at a potential suitable for the production of elemental hydrogen. In one embodiment of the present invention, the metal component with higher activity in oxidation by water is selected from the group of magnesium, calcium, strontium, barium, aluminum, gallium and mixtures thereof. In another embodiment of the invention, the metal component with lower activity in oxidation by water is a member of groups 3 through 12 of the periodic table of elements. In a preferred embodiment the metal component with lower activity in oxidation by water is selected from the group consisting of iron, cobalt, nickel, titanium, palladium, platinum, manganese, and mixtures thereof.

In a preferred embodiment, the metal components are intimately mixed by exposing the metal components to a temperature high enough to melt one component but not the other.

In yet another embodiment of the invention, the providing of hydrogen for the treatment of contaminated soil is coupled to electrokinetic based bioremediation techniques.

The present invention also provides for the coupling of soil treatment of contaminated soils by providing hydrogen and remediation systems that include soil venting.

The present invention also provides for the coupling of soil treatment of contaminated soils by providing hydrogen and remediation systems that include the insertion of physical barriers.

The present invention encompasses the treatment of organic contaminants that contain an aromatic moiety.

The techniques and methods disclosed in the present application can be effectively used in the removal of a variety of contaminants from contaminated soils. Without limiting the scope of the present invention, chlorinated organic compounds such as chlorinated ethene having the formula $C_2Cl_xH_{(4-x)}$ (x=1, 2, 3, or 4) are particularly suited for removal by the techniques of the invention. Other contaminants that can be effectively removed from the soil and other contaminated environments comprise chlorinated organic compounds that are partially or fully chlorinated such as aliphatic compounds having the formula $C_nCl_xH_{((2n+2)-x)}$ ($1 \leq x \leq 2n+2$, $n \geq 1$).

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The invention is a method for enhancing the biodegradation of chlorinated organic compounds in the ground by naturally occurring bacteria through the use of hydrogen as an electron donor. Also part of this invention are means for generating and delivering the required hydrogen to the contaminated environments.

Figure 4:
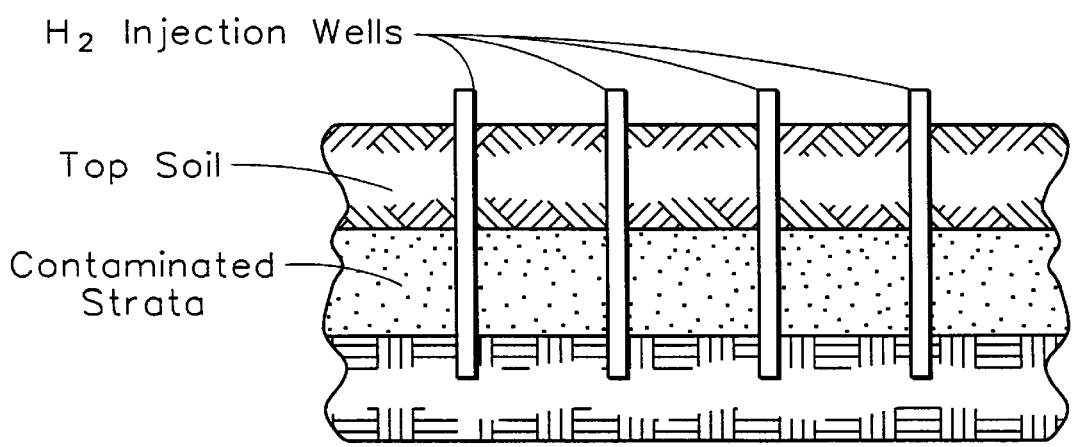
FIG. 4 is a schematic diagram depicting direct injection into the soil of hydrogen from a variety of sources.

FIG. 4 is a schematic diagram illustrating one aspect of the invention comprising injecting hydrogen gas directly from the surface into the contaminated region. In some embodiments, hydrogen delivery may be coupled with other applications. Direct injection of hydrogen requires inserting a number of narrow tubes into the ground for the injection of gas. The volume of gas handled must be small enough to avoid the undesirable return of gas to the surface. Any hydrogen that does return to the surface represents lost reducing potential.

The advantage of providing the hydrogen directly to the soil is that it permits very precise control of the amount of hydrogen delivered to the soil. Another advantage is that hydrogen can be supplied from a variety of sources. It can be delivered to the location of treatment as a compressed gas and fed directly into the wells. It can also be generated at the location where it is needed. In locations where electric power is readily available, hydrogen can be generated on demand by electrolysis. If electric power is not readily available, hydrogen can be generated by reforming hydrocarbons that can be delivered to the site by truck or pipeline.

Generating the hydrogen directly in the soil, in immediate access to the contaminants in the soil can be greatly advantageous. Some of these advantages include a more efficient use of the hydrogen, most of the hydrogen generated in situ would be either used in the soil or stored in the soil for future use. Other advantages include the elimination of costly human involvement in monitoring the delivery of hydrogen to the soil from external sources. In situ generation of hydrogen in the soil can be accomplished in several ways.

In one embodiment of the present invention, in situ production of hydrogen is coupled to electrokinetic remediation. In electrokinetic remediation processes, electrodes are inserted in the soil, and application of an electric field causes reactions to occur at the electrodes. In this technique, two (or more) wells are drilled into the ground to a depth adequate to access the contaminated layer. Electrodes are placed in the wells and a direct current is applied between the electrodes, generating electric fields up to 100 V/m, the electric field may be DC, AC, pulsed fields, combinations thereof or any other waveform.

Figure 1:
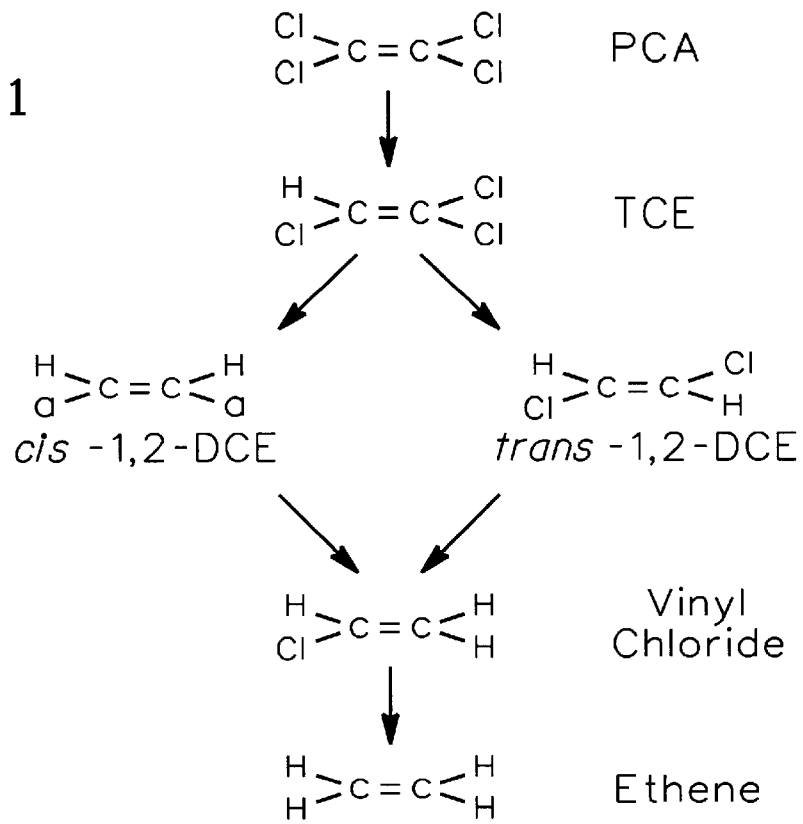
FIG. 1 is a schematic illustration of the degradation pathway for perchloroethylene to ethylene.
Figure 2:
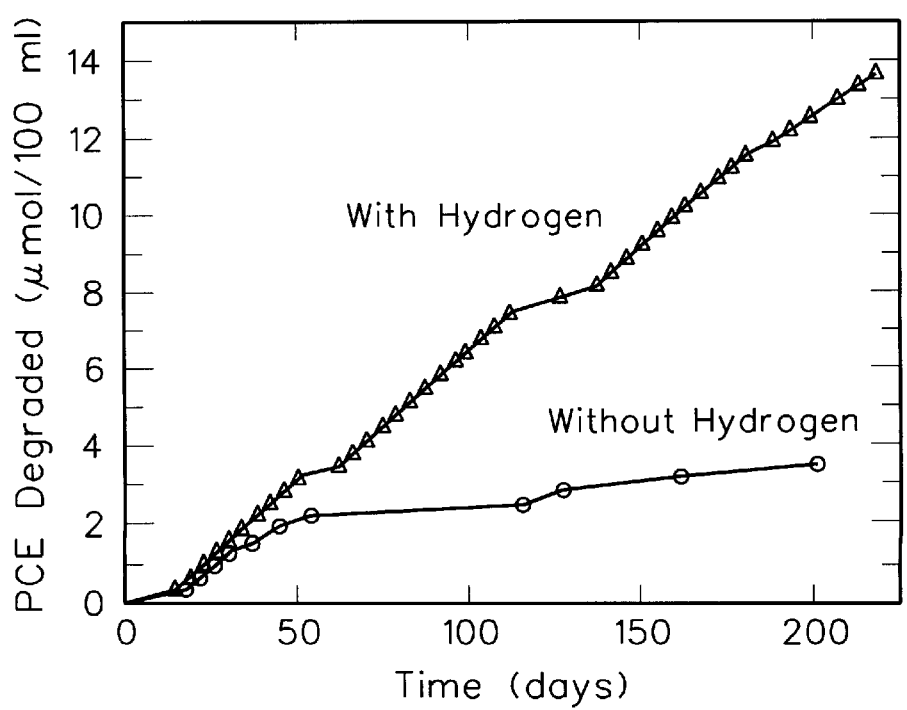
FIG. 2 is a graph showing the effect of added hydrogen on PCE degradation.
Figure 3:
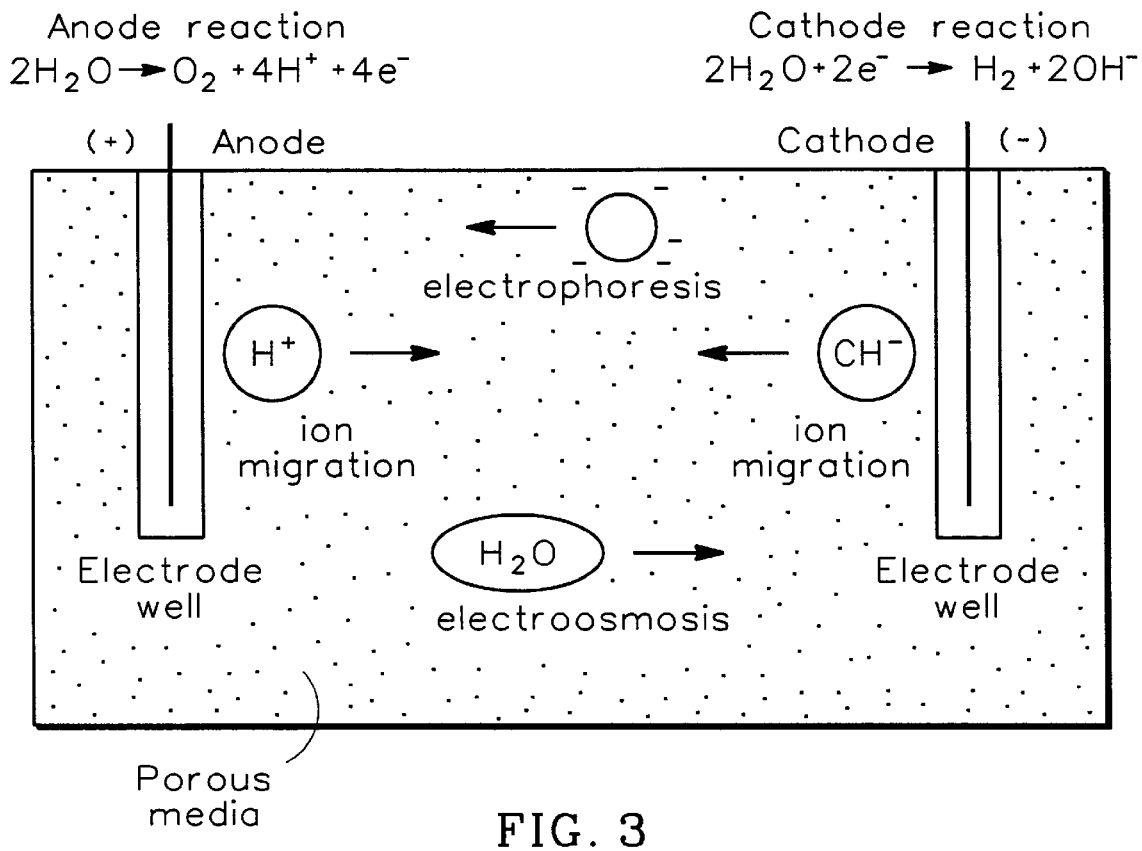
FIG. 3 is a schematic diagram illustrating the movement of charged and uncharged species through porous media by electrokinetics.

FIG. 3 is a schematic diagram illustrating the basic processes underlying the application of electrokinetic methods to bioremediation. When the current is applied a number of processes occur. Water is electrolyzed with oxygen and protons formed at the anodes and hydrogen and hydroxyl ions formed at the cathodes. The electric field causes cations to migrate towards the cathode and anions to migrate towards the anode. The ions carry their water of hydration with them, and since cations generally have a higher hydration than anions, this produces a net electroosmotic flow towards the cathode. Particles that have a net charge migrate electrophoretically in the same direction as ions with the same sign. The ion migration splits dissolved salts and moves them into the water in the well where they can be removed with the water. The electrophoretic motion gradually removes colloidal particulates as well. As these actions occur, the soil pH is altered, with the region around the cathode becoming more basic and the region around the anode becoming acidic. This can be alleviated by adding acid or base to the water in the electrode wells, as needed, with care taken to insure that the acids and bases used will not contribute to the problem being remediated. The hydrogen and oxygen being generated can be re-injected into the soil to promote aerobic and anaerobic bacterial growth respectively.

Electrokinetic techniques are also used to deliver nutrients to microbial communities living in the soil. This approach enhances the rate of growth of organisms degrading pollutants and consequently accelerates the degradation processes. The electrodes used in conjunction with this invention may be positioned directly in the soil or inserted into wells or within trenches in the soil. The electrodes may have a variety of shapes, rods or flat sheets are examples of electrodes that can be used in this invention. The wells may have a variety of geometries as well. In any particular case, a multiplicity of anode and cathode pairs may be used. In this invention, it is possible to simultaneously use dozens of electrodes at a single site. The invention specifically includes the use of unequal numbers of anodes and cathodes, such as a single anode surrounded by four cathodes.

At the electrodes, oxygen (at the anodes) and hydrogen (at the cathodes) are evolved during the electrokinetic process. The gases can be utilized in a variety of ways. One way of utilizing the gases is to keep the well sealed, especially if the well is cased for some distance below the soil surface. As the gas is evolved, its partial pressure rises which results in increasing solubility. This leads to a greater concentration of gas in the solution present in and near the well bore, and a concomitant diffusion of dissolved gas away from the well and into the soil, where it is available to microorganisms. If the gas is evolved too rapidly, it may be necessary to bleed part of it out of the well. In this situation, regulation of the pressure inside the well permits control of the concentration of gas in the water. Regulation of the pressure inside the wells can be combined with volumetric measurements of the amount of gas released, and be used to determine how much gas is passing into the soil, since the total amount of gas evolved can be calculated from the applied current.

The gases can be trapped and collected during the generating process. The gas is recovered by either allowing it to come out of solution in the well and rise to the surface as bubbles, where it is collected, or by circulating the solution from the bottom of the well to the surface. In the latter case, some of the gas spontaneously comes out of solution in the well, and is removed as bubbles in the liquid stream and some of the gas comes out of solution as the pressure is released during the solution's rise to the surface. The gas that remains in solution at the surface is largely removed by heating the solution to reduce the solubility of the gas and promote its separation.

Trapped or collected hydrogen is fed into the soil through gas injection tubes or gas distribution tubes. Many gas injection tubes can be used and their position and spacing of the tubes relative to each other can vary. As noted, the method includes a means of removing fluids from around the positive or negative electrodes. The operation includes a method for re-introducing or feeding fluids into the area around the electrodes. Solutions that are being re-circulated can be held in storage tanks for short or long periods of time. The fluids introduced to the regions around the electrodes can be supplemented with compounds that sustain the reactions of soil organisms. Some of the compounds that can be used in conjunction with the present invention include acetic acid, lactic acid, butyric acid, propionic acid, citric acid, toluene, yeast or other biological extracts. The mixture may also contain inorganic forms of, for example, phosphorus and nitrogen.

In cases where it is important to maintain the soil environment in either an aerobic or anaerobic condition, it is desirable to selectively remove from the soil as much of one of the gases being generated as possible, while insuring that as much as possible of the other gas is kept in the soil. For example, there are situations where it is desirable to keep as much hydrogen in the soil as possible, while disposing of the oxygen. In this case, optimal results are obtained when the cathodes are kept sealed, with back pressure regulators connected to the casings. When the pressure inside the well exceeds the regulated pressure, the excess gas is bled off and fed to a gas injection tube located some distance away insuring that all of the hydrogen is retained in the soil. The anodes are left open to the air, and the oxygen content of the water in the anode well is minimized, for example by pumping and recirculating the water continuously.

Figure 5:
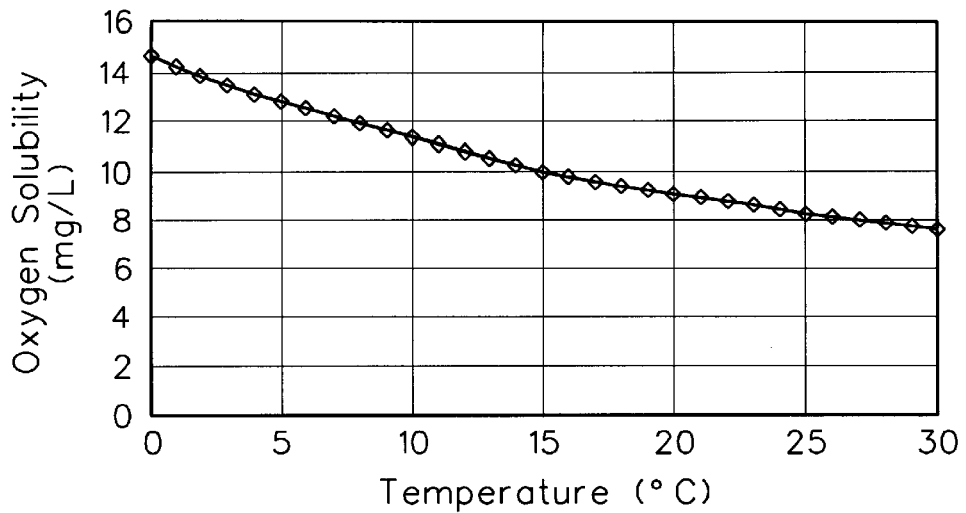
FIG. 5 is a graph showing the evolution of solubility of oxygen in water as a function of temperature for water in equilibrium with air.

FIG. 5 is a graph showing the evolution of solubility of oxygen in water as a function of temperature for water in equilibrium with air. To insure that as much of the oxygen as possible is removed from the solution on each cycle, the water can be heated. Since the solubility of oxygen in water declines with increasing temperature a further reduction in oxygen content in the recirculated water is achieved.

Those skilled in the art will appreciate that there are many other chemical agents that can be added for the purposes of promoting the activity of soil microorganisms. Fatty acids such as butyric, lactic or propionic acid are used as electron donors for enhancement of the dechlorination process and are added to the soil through the electrode wells. These acids serve in the cathode wells as well to neutralize the well solution pH.

As described above, applying an electric field causes various electrokinetic phenomena, such as electromigration and electroosmosis, to occur in the soil. These induce a horizontal transport of pore fluid which causes the added hydrogen gas and other electron donors to migrate between the electrodes in an electric field, effectively spreading them away from the well bore. The electrokinetic transport of nutrients and electron donors and acceptors into the soil is utilized to enhance the growth of indigenous microorganisms which are capable of destructing trichloroethylene, a prominent soil contaminant.

As a consequence of the electrochemical splitting of water at the electrodes, low pH is developed in the anode wells during the process and high pH in the cathode wells. To keep the solutions at a neutral pH, the solutions from wells of opposite polarity are frequently pumped and mixed in the mixing tank. The pH can also be controlled by adding to the solution a base or an acid such as citric acid. When citric acid is added, it can also serve as a carbon source for microorganisms in the mixing tank. Thus, when citrates are transported through the soil by electroosmosis from the anode toward the cathode wells or by electromigration from the cathode toward the anode wells they can serve as an additional reductant. If necessary, to keep the mixing tank and electrode well solutions at neutral pH, a dilute solution of sodium hydroxide may be used for decreasing pH in the mixing tank and electrode wells.

During the process described above, the soil temperature is slightly enhanced, and can be controlled by the power supply, i.e., by controlling the current passed through the soil. Increased soil temperature (ca 30–35° C.) is beneficially used to further enhance the growth of the indigenous microorganisms in soil.

The invention also allows complex procedures where both the anaerobic and aerobic biodegradation processes are enhanced in the soil. For example, the enhancement of the anaerobic process may be pursued at the site, by introducing hydrogen and other electron donors such as butyrates as electron donors and citric acid as a carbon source. The anaerobic process preferentially dechlorinates trichloroethylene to dichloroethenes and vinyl chloride. Subsequently, aerobic biodegradation may be enhanced by introducing electrochemically produced oxygen at the anode wells in the soil. Oxygen is distributed through out the soil by electroosmotic flow and diffusion. This process is used for the dechlorination of dichloroethylene and vinyl chloride at the site, i.e., to provide a full biomineralization of DNAPLs (dense non-aqueous phase liquids) present at the site. When the thermal process does not reduce the oxygen content of the water sufficiently, anaerobic processes are further enhanced by the addition of environmentally benign reducing agents, such as sodium meta-bisulfite ($Na_2S_2O_5$, disodium salt of pyrosulfurous acid) in the mixing tank. Due to the oxidation of bisulfite by oxygen to sulfates, no harmful chemicals are introduced in the soil.

In another embodiment of the present invention, hydrogen is produced in situ through corrosion reactions of metal particles that are used to produce hydrogen. Hydrogen then serves as an electron donor for anaerobic microorganisms capable of transforming chlorinated organic compounds, such as chlorinated ethenes, into benign end products.

Sites contaminated with chlorinated ethenes are often populated by microbial communities adapted to the soil's contaminated condition. However, degradation of the contaminants is generally slow due to limited supply of reducing equivalents.

In one aspect of this invention, metal particles composed of iron and magnesium, of sufficiently small size (30 $\mu$m or less) are introduced into the ground water at an injection point.

Figure 6:
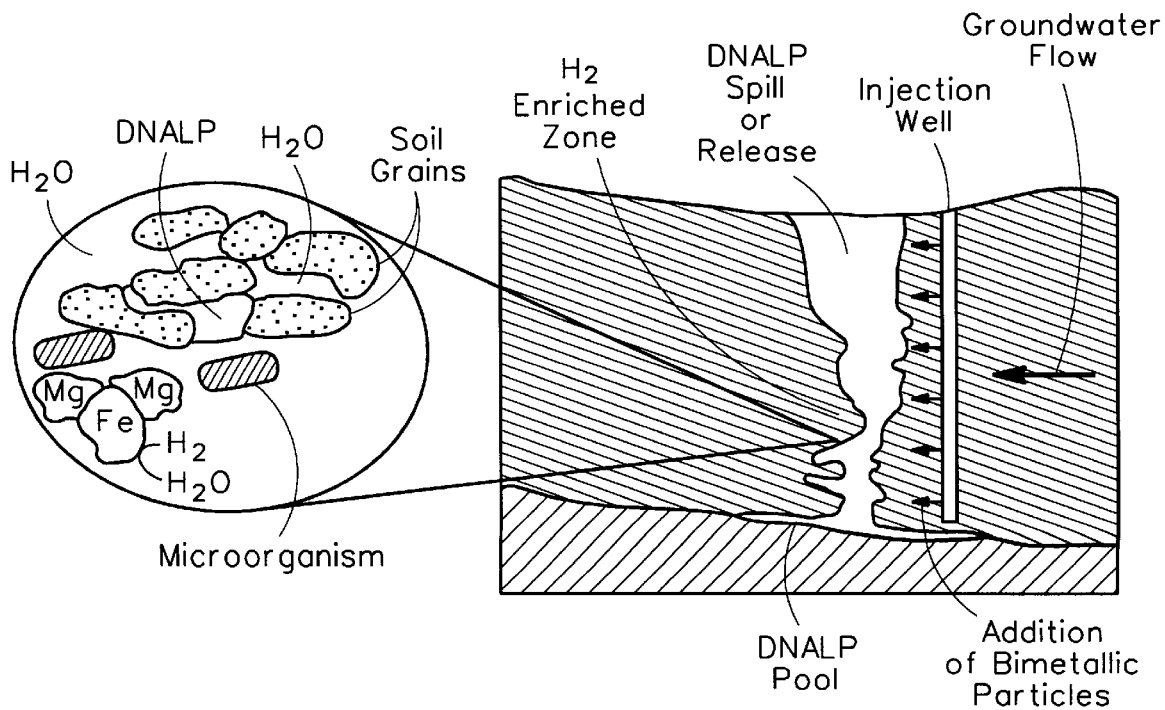
FIG. 6 is a schematic depiction of the principal of passive hydrogen enrichment using bimetallic particles.

FIG. 6 is a schematic diagram illustrating the concept of passive hydrogen enrichment using bimetalic particles. In contact with water, corrosion reactions occur leading to the formation of hydrogen at the surface of the metal. The formed hydrogen diffuses freely, creating a reaction zone around the metal particles that is supplemented with a potential electron donor. The method is applied directly at or around the source of contamination.

Figure 7:
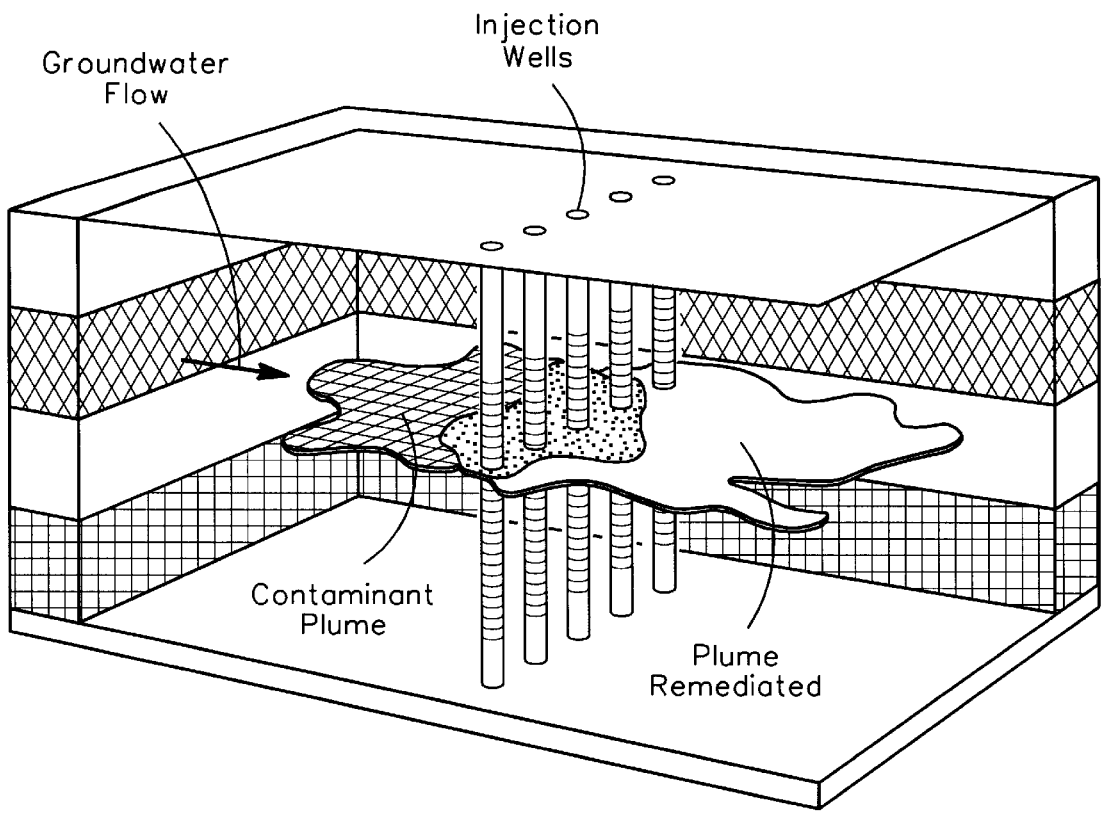
FIG. 7 is schematic diagram depicting the concept of using a passive "anaerobic barrier".

FIG. 7 is a schematic diagram illustrating the concept of using a passive "anaerobic barrier". In this technique, the barrier helps in limiting the spread of the contaminant and/or remove it from ground water leaving the site.

In contrast to previous uses of zero-valent iron, where the hydrogen formation reaction (see equation 4, which is the net reaction produced by combining equations 1 and 3) is a "parasitic side reaction," in this invention, hydrogen generation is coupled to dechlorination through biocatalytic processes. Although direct dechlorination reactions may still occur at the iron-solution interface, this reaction is unlikely to be significant in changing the concentration of toxicant present in the soil because of the small amount of reactive surface area available when compared to the volume of the soil permeated by the hydrogen produced.

$$Fe^\circ + 2H_2O \rightarrow H_2(g) + Fe^{2+} + 2OH^- \quad (4)$$

Figure 8:
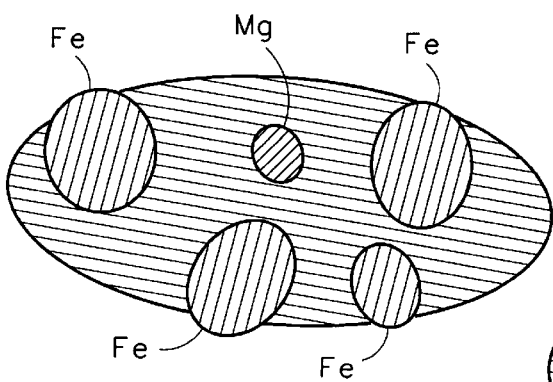
FIG. 8 is a drawing of one example of bimetallic particles that can be used in conjunction with this invention.

FIG. 8 is a drawing of one example of bimetallic particles that can be used in conjunction with this invention. The driving force of the reaction is a corrosion reaction, which consists of several partial steps.

Anodic metal dissolution:

$$Mg \rightarrow Mg^{2+} + 2e^- \quad E^\circ = -2.363 \text{ V} \quad (5)$$

provides electrons for the reduction reaction occurring as:

$$2H_2O + 2e^- \rightarrow H_2 + 2OH^- \quad E^\circ = -0.420 \text{ V} \quad (6)$$

The overall reaction is:

$$Mg + 2H_2O \rightarrow H_2 + Mg(OH)_2 \quad E_{cell} = -1.943 \text{ V} \quad (7)$$

In the "managed" production of hydrogen, water-induced corrosion leading to an inactive iron hydroxide surface (e.g., eq. 8) is avoided because the iron surface is corrosion protected by the magnesium, which functions as a sacrificial anode.

$$Fe^{2+} + 2H_2O \rightarrow Fe(OH)_2 + 2H^+ \quad (8)$$

$$Fe + 2H^+ \rightarrow Fe^{2+} + H_2 \quad (9)$$

However, as the Mg becomes depleted the reactions shown in both equations 8 and 9 may occur, where the latter equation being advantageous in that it too forms hydrogen.

Another factor that can affect $H_2$ production is the use of an electrocatalyst. Table 1 shows the exchange current densities for the $H_2$ evolution reaction on various metals in acid media. Exchange current density ($i_o$) is an indication of how far away from the equilibrium or reversible potential the system must be, (i.e., what overpotential must be applied) for $H_2$ evolution to occur at a given rate. The lower the value of $i_o$ the more difficult it is for the reaction to occur, hence a greater overpotential is needed. From Table I it can be seen that iron is a relatively poor $H_2$ forming metal.

Figure 9:
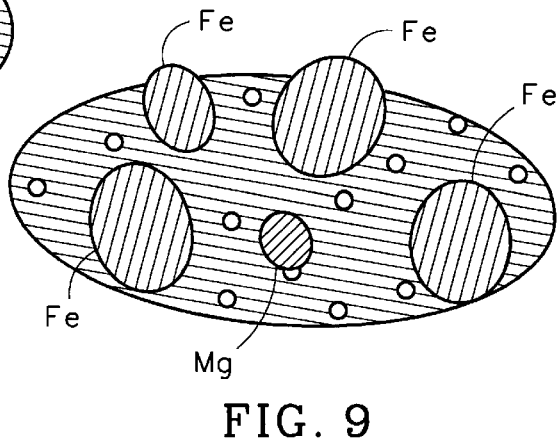
FIG. 9 is a drawing of a particle similar to the particle depicted in FIG. 8 illustrating the addition of a small amount of a third metal.

FIG. 9 is a drawing of a particle similar to the particle depicted in FIG. 8 illustrating the addition of a small amount of a third metal. Hydrogen formation can be substantially improved by catalyzing the surface of iron with small deposits of metals, such as palladium (Pd) or nickel (Ni), which have relatively high $i_o$ for hydrogen formation. This approach has to be weighed, however, against the increased costs associated with the use of metals such as Pd and the potential for increased toxicity through the use of metals like Ni. This approach may also bring about improved rates of reductive dechlorination with difficult to degrade contaminants which are most effectively degraded at the metal-solution interface, another aspect of the present invention.

TABLE I

Approximate Exchange Current Densities for the Hydrogen Evolution Reaction on Various Metals in $H_2SO_4$.

| Metal | $i_o$ (A/m$^2$) |
|---|---|
| Hg | $10^{-8.2}$ |
| Cd | $10^{-6.9}$ |
| Fe | $10^{-5.0}$ |
| Ti | $10^{-4.2}$ |
| Nb | $10^{-3.0}$ |
| W | $10^{-2.0}$ |
| Au | $10^{-1.5}$ |
| Ni | $10^{-1.2}$ |
| Rh, Ir | $10^{+0.3}$ |
| Pd, Pt | $10^{+0.9}$ |

The bimetallic particles used in this invention can be distributed in the soil in a number of ways. These include, but are not limited to, directly distributing loose particles freely in the soil by placing them in a trench, which is back filled on top of them, injecting them into holes or wells which may be closed, or left open and used for fluid removal. They may also be packaged into porous filter "socks" made of high density polyethylene, PTFE, or other non-degradable polymers. Contact with the ground water can be made by placing these socks in wells or trenches and the hydroxide residue produced removed after the treatment is complete.

Some of the key advantages of this invention, particularly of using bimetallic particles as hydrogen sources for soil remediation are listed below.

1. The invention provides an in situ treatment method with minimal environmental impact. No excavation is required and the materials transferred to the soil are environmentally benign. Note that the degradation products produced by the corrosion of the metal particles, such as iron and magnesium hydroxides and oxides, are environmentally benign and, in fact, are both naturally occurring in significant concentrations in soil.
2. The cost of the materials used in this invention is low because a high percentage of the reductant formed can be coupled to reductive dechlorination, mediated by hydrogen.
3. A passive long term remediation source is provided with little or no maintenance required.
4. The bimetallic particles used in conjunction with this invention can be stored almost indefinitely before use.
5. Hydrogen is introduced into the system without volatilization of the pollutants.
6. The particles can be introduced at any point in the soil to provide a barrier treatment zone without the need for expensive fixed bed installations.
7. The particles can be used as redox control agents.
8. The methods do not disturb the flow pattern of the contaminant plume.
9. High potential for hydrogen delivery at a rate and concentration suited to metabolic uptake by dechlorinating microorganisms.

Another aspect of the invention is to accompany the reducing agent (electron donor) with an oxidizing agent to insure oxygenation of the soil and support aerobic processes. Oxygenation may be made through aeration and sparging procedures.

Oxygen release compounds (ORC-) can also be used. The method presented in this invention enhances aerobic clean-up by creating oxygen rich regions in the soil. Oxygen is often the limiting factor in aerobic bioremediation, whereas nutrients such as phosphorus and nitrogen are generally present in sufficient quantities. The ORC compounds may include a formulation of very fine insoluble peroxygen that releases oxygen at a slow, controlled rate when hydrated. These compounds release oxygen when they come into contact with water as shown below.

$$2MgO_2 + 2H_2O \rightarrow O_2 + 2Mg(OH)_2 \qquad (10)$$

The final product is magnesium hydroxide making the ORC environmentally safe to use. The oxygen release profiles of the formulations are controlled by small amounts of simple phosphates intercalated into the solid $MgO_2$ crystal structure. Implementation of ORC can be achieved through several techniques. One technique consists in packaging the ORC into porous filter "socks" made of high density polyethylene. Contact with the ground water can be made by placing these socks in wells or trenches. The ORC can also be dispersed as free powder.

One procedure for making the iron-magnesium bimetallic particles takes advantage of the differences between certain physical properties of iron and magnesium. Iron has a density of 7.87 g cm$^{-3}$ and a melting point of 1538° C. The corresponding values for magnesium are 1.74 g cm$^{-3}$ and 650° C.

One source of iron used in conjunction with the present invention provides three lots of iron powders available from Johnson Matthey having average particle sizes of 74 $\mu$m, 44 $\mu$m, and 10 $\mu$m and purity of greater than 98% (on a metals basis). Each lot of iron powder may be degreased and cleaned by ultrasonication in a commercial detergent solution followed by washing in deionized water. Subsequently, the iron is deoxidized by ultrasonication in a commercial deoxidizer solution. The iron powders should then be ultrasonicated in deionized water, dried in a stream of dry air and stored in a dessicator under an inert atmosphere.

An alternative iron source is the iron sold commercially for use as recording pigment on high coercivity recording tapes. This high surface area iron is free of contaminants and oxides eliminating the need for any pretreatment steps. It has two drawbacks however, because of its small particle size it is pyrophoric, requiring special handling under an inert atmosphere and it is substantially more expensive.

Magnesium granules (99.8% purity on metals basis) are also available from Johnson Matthey. A predetermined amount of the granules are placed in a crucible, not wetted or reactive with molten magnesium. An appropriate amount of one of the grades of iron powders is then added to the magnesium granules in the crucible. In conjunction with the present invention, it is possible to use a wide variety of volumetric ratios of solid iron powder to molten magnesium metal. The crucible is then placed in a vertical furnace equipped with provision for maintaining an inert gas environment. The furnace is heated to 750° C. which is well above the melting point of magnesium, but well below the melting point of iron. Any residual oxide film on the surface of the iron particles is removed by reaction with the molten magnesium by the simple reaction shown in equation 11. This reaction, as written, is exothermal to the extent of 88.84 kcal per mole of $Fe_2O_3$.

$$Fe_2O_3 + 3Mg \rightarrow 3MgO + 2Fe \qquad (11)$$

Because the temperature of the furnace is maintained well below the melting point of iron, no significant alloying of magnesium with iron takes place. The iron powder settles at the bottom of the crucible due to the much greater density of iron compared to magnesium. Thus, at a low volume fraction of iron it is necessary to keep the iron particles suspended in the molten magnesium. This is accomplished by rapidly stirring the contents of the crucible followed by rapidly cooling the furnace to give rise to a homogeneous dispersion of iron particles in the solidified magnesium matrix. At high iron volume fractions stirring is not necessary.

Subsequent to cooling, the resulting bimetallic ingot is removed from the crucible and placed in a mill to be crushed. Again, for safety reasons, the crushing operation is carried out in an inert gas environment. Ball milling and sieving may also be included to obtain iron-magnesium particles in the desired size range. After the crushing/milling operation, the particles comprise surfaces that expose both iron and magnesium to the environment. The recovered iron-magnesium bimetallic particles are stored with precautions taken to protect them from moisture, since the addition of moisture favors hydrolysis. It is preferred that the particles remain protected by maintaining them in an inert atmosphere until they are used.

EXAMPLE (HYPOTHETICAL)

The following example shows the function of this invention and some of its preferred embodiments as to the manufacture of bimetallic metal particles:

Approximately 8 g of finely powder iron (−325 mesh) was added to a similar amount of magnesium chips (1 to 5 mm) in an alumina ($Al_2O_3$) crucible. The crucible was placed in an oven equipped for purging with argon and to permit the connection of an argon stirrer. The second argon connection, the stirrer, is connected via a stainless steel flex line to a quartz tube that is placed in the crucible with its exit near the bottom. After purging thoroughly, the furnace was heated to 700° C. to melt the magnesium. A short time after the furnace reached 700° C., the stirring gas was turned on to mix the melt and the heat was turned off. The stirring flow was continued as the metal cooled until the stirring gas flow became blocked by the solidification of the metal. After the ingot had cooled to a temperature of 95° C. the furnace was opened and the ingot was removed and transferred to an argon purged dry box. The ingot was crushed using a steel mortar and pestle. The crushed material was sieved. Material passing through a standard 200 mesh sieve was removed for use and the coarser material recrushed. All of the fine material was sealed in a bottle in the dry argon atmosphere to insure that no corrosion took place before use.

While the foregoing is directed to the preferred embodiment of the present invention, other and further embodiments of the invention may be devised without departing from the basic scope thereof, and the scope thereof is determined by the claims which follow.

What is claimed is:

1. A method for enhancing the rate of biodegradation of chlorinated organic compounds in contaminated environments comprising:

providing hydrogen to the environment; and
transporting one or more organic electron donors into the environment by electrokinetics, wherein the one or more organic electron donors are selected from glucose, methanol, ethanol, toluene, dichloromethane, an acid, a salt of the acid and mixtures thereof, wherein the acid is selected from acetic acid, formic acid, lactic acid, benzoic acid, propionic acid, crotonic acid, and butyric acid.

2. The method of claim 1 wherein the contaminated environment is contaminated soil.

3. The method of claim 2 wherein the hydrogen is provided by an above ground hydrogen source.

4. The method of claim 3 wherein the above ground hydrogen source comprises a gas storage system.

5. The method of claim 3 wherein the above ground hydrogen source comprises a hydrogen generator.

6. The method of claim 5 wherein the hydrogen generator is an electrochemical device.

7. The method of claim 6 wherein the electrochemical device is an electrolyzer.

8. The method of claim 5 wherein the hydrogen generator is a carbonaceous fuel reforming system.

9. The method of claim 8 wherein the reforming system is a steam reformer.

10. The method of claim 8 wherein the reforming system is a partial combustion cracker.

11. The method of claim 8 wherein the reforming system is an autothermal reformer.

12. The method of claim 8 wherein the carbonaceous fuel is produced by degradation of waste materials.

13. The method of claim 2 wherein the hydrogen is generated in the soil.

14. The method of claim 13 wherein the hydrogen is generated electrochemically by supplying an electric current to the soil.

15. The method of claim 13 wherein the hydrogen is generated by corroding metal particles inserted in the soil.

16. The method of claim 15 wherein the metal particle consists of two or more metals.

17. The method of claim 16 wherein the metal particles comprise at least two metal particles with different activities in oxidation by water; wherein a first metal particle has a higher activity in oxidation by water and a second metal particle has a lower activity in oxidation by water.

18. The method of claim 17 further comprising the step of contacting the metal particle with water or electrolytes containing water.

19. The method of claim 18 wherein the metal particle with higher activity in oxidation by water is corroded causing the metal particle with lower activity in oxidation by water to be at a potential suitable for the production of elemental hydrogen.

20. The method of claim 19 wherein the metal particle with higher activity in oxidation by water is selected from the group consisting of magnesium, calcium, strontium, barium, aluminum, and gallium.

21. The method of claim 19 wherein the metal particle with lower activity in oxidation by water is a member of groups 3 through 12 of the periodic table of elements.

22. The method of claim 19 wherein the metal particle with lower activity in oxidation by water is selected from the group consisting of iron, cobalt, nickel, titanium, palladium, platinum, and manganese.

23. The method of claim 15 further comprising the step of loosely dispersing the metal particles in the soil.

24. The method of claim 15 wherein the metal particles are retained in a porous medium.

25. The method of claim 15 further comprising the step of introducing the metal particles into the soil by electrokinetics.

26. The method of claim 2 further comprising venting hydrogen from the soil.

27. The method of claim 2 further comprising the insertion of physical barriers into the environment.

28. The method of claim 1 wherein the chlorinated organic compound comprises at least one aromatic moiety.

29. The method of claim 1 wherein the chlorinated compound is a poly-chloro-biphenyl compound.

30. The method of claim 1 where the chlorinated organic compound is a chlorinated ethene having the formula $C_2Cl_xH_{(4-x)}$ (x=1, 2, 3, or 4).

31. The method of claim 1 where the chlorinated organic compound is a partially or fully chlorinated aliphatic compound having the formula:

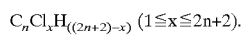

$$C_nCl_xH_{((2n+2)-x)}\ (1 \leq x \leq 2n+2).$$

32. The method of claim 1, further comprising:

dissolving the hydrogen and the organic electron donor in water and delivering the water into the environment by electroosmosis.

33. The method of claim 1, further comprising the step of electrokinetically delivering nutrients into the soil.

34. The method of claim 1, further comprising the steps of:

providing an anode well and a cathode well into the environment; and adding fatty acids or salts of the fatty acids to the cathode well.

35. The method of claim 1, further comprising the step of adding citric acid to the environment.

36. The method of claim 1, further comprising the step of:

stopping the provision of hydrogen to the environment; then delivering oxygen to the environment; and stimulating aerobic growth of microorganisms in the environment.

37. The method of claim 1, further comprising the step of:

increasing the temperature of the environment by passing electrical current through the environment.

38. The method of claim 1, wherein the organic electron donor is delivered to the environment by electromigration.

39. The method of claim 1, wherein the organic electron donor is delivered to the environment by electrophoresis.

40. A method for enhancing the rate of biodegradation of chlorinated organic compounds in contaminated environments comprising:

dissolving hydrogen and at least one organic electron donor in water, wherein the at least one organic electron donor is selected from glucose, methanol, ethanol, toluene, dichloromethane, an acid, a salt of the acid and mixtures thereof, wherein the acid is selected from acetic acid, formic acid, lactic acid, benzoic acid, propionic acid, crotonic acid, and butyric acid; and delivering the water into the environment by electroosmosis.

41. The method of claim 40, further comprising the step of electrokinetically delivering nutrients into the soil.

42. A method for enhancing the rate of biodegradation of chlorinated organic compounds in a contaminated environment comprising:

generating hydrogen in situ;

dissolving at least one organic electron donor in water, wherein the at least one organic electron donor is selected from glucose, methanol, ethanol, toluene, dichloromethane, an acid, a salt of the acid and mixtures thereof, wherein the acid is selected from acetic acid, formic acid, lactic acid, benzoic acid, propionic acid, crotonic acid, and butyric acid; and delivering the water into the environment by electroosmosis.

43. The method of claim 42, wherein the step of generating hydrogen includes corroding metal particles dispersed in the soil.

44. The method of claim 42, further comprising the step of electrokinetically delivering nutrients into the soil.

* * * * *